(12) United States Patent
Meyer

(10) Patent No.: US 11,534,279 B2
(45) Date of Patent: Dec. 27, 2022

(54) METHOD FOR PRODUCING DENTURES

(71) Applicant: bredent GmbH & Co. KG, Senden (DE)

(72) Inventor: Joachim Meyer, Ulm (DE)

(73) Assignee: bredent GmbH & Co. KG, Senden (DE)

( * ) Notice: Subject to any disclaimer, the term of this patent is extended or adjusted under 35 U.S.C. 154(b) by 743 days.

(21) Appl. No.: 16/303,319

(22) PCT Filed: May 23, 2017

(86) PCT No.: PCT/EP2017/062469
§ 371 (c)(1),
(2) Date: Nov. 20, 2018

(87) PCT Pub. No.: WO2017/202869
PCT Pub. Date: Nov. 30, 2017

(65) Prior Publication Data
US 2019/0209276 A1    Jul. 11, 2019

(30) Foreign Application Priority Data

May 23, 2016   (DE) ...................... 10 2016 109 447.1
May 23, 2016   (DE) ...................... 10 2016 109 449.1

(51) Int. Cl.
| | |
|---|---|
| *A61C 13/083* | (2006.01) |
| *C04B 35/64* | (2006.01) |
| *A61C 5/20* | (2017.01) |
| *A61K 6/802* | (2020.01) |
| *B28B 1/14* | (2006.01) |

(52) U.S. Cl.
CPC .............. *A61C 13/083* (2013.01); *A61C 5/20* (2017.02); *A61K 6/802* (2020.01); *B28B 1/14* (2013.01); *C04B 35/64* (2013.01); *C04B 2235/616* (2013.01)

(58) Field of Classification Search
CPC .. A61C 13/083; C04B 35/64; C04B 2235/616
See application file for complete search history.

(56) References Cited

U.S. PATENT DOCUMENTS

| | | | | |
|---|---|---|---|---|
| 4,433,959 A | * | 2/1984 | Faunce ................... | A61C 5/20 106/35 |
| 5,346,397 A | | 9/1994 | Braiman | |

(Continued)

FOREIGN PATENT DOCUMENTS

| | | |
|---|---|---|
| CA | 2 287 083 A1 | 5/2000 |
| DE | 35 24 783 A1 | 1/1987 |

(Continued)

OTHER PUBLICATIONS

International Search Report of PCT/EP2017/062467, dated Aug. 7, 2017.

(Continued)

*Primary Examiner* — Erin Snelting
(74) *Attorney, Agent, or Firm* — Collard & Roe, P.C.

(57) ABSTRACT

A method for producing dentures uses a green compact containing a mixture of ceramic powder and a binder system. A ceramic shell for dentures can be produced from the green compact and can be shaped and can be adapted to a carrier prior to a firing step below a temperature of 1050° C.

13 Claims, 1 Drawing Sheet

(56) References Cited

U.S. PATENT DOCUMENTS

| | | | | |
|---|---|---|---|---|
| 5,910,273 | A | * | 6/1999 | Thiel ................ A61C 13/0003 |
| | | | | 264/16 |
| 6,183,256 | B1 | * | 2/2001 | Fisher .................... A61C 5/30 |
| | | | | 433/218 |
| 6,921,500 | B1 | | 7/2005 | Feenstra |
| 9,132,067 | B2 | | 9/2015 | Glueck et al. |
| 2004/0245663 | A1 | | 12/2004 | MacDougald et al. |
| 2006/0118990 | A1 | | 6/2006 | Dierkes et al. |
| 2009/0026643 | A1 | | 1/2009 | Wiest et al. |
| 2009/0035726 | A1 | | 2/2009 | Bozdemir |
| 2017/0035537 | A1 | * | 2/2017 | Leeson .................. C04B 35/48 |
| 2019/0209275 | A1 | | 7/2019 | Meyer |

FOREIGN PATENT DOCUMENTS

| | | |
|---|---|---|
| DE | 295 06 554 U1 | 9/1995 |
| DE | 600 23 315 T2 | 8/2006 |
| DE | 10 2006 034 551 A1 | 1/2008 |
| DE | 10 2009 051 593 A1 | 5/2011 |
| DE | 10 2016 109 447 A1 | 12/2017 |
| EP | 0 826 642 A2 | 3/1998 |
| EP | 0 998 882 A2 | 5/2000 |
| WO | 2007/028787 A1 | 3/2007 |

OTHER PUBLICATIONS

International Search Report of PCT/EP2017/062469, dated Aug. 14, 2017.

\* cited by examiner

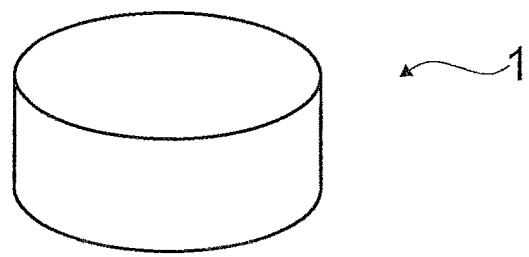
Fig. 1
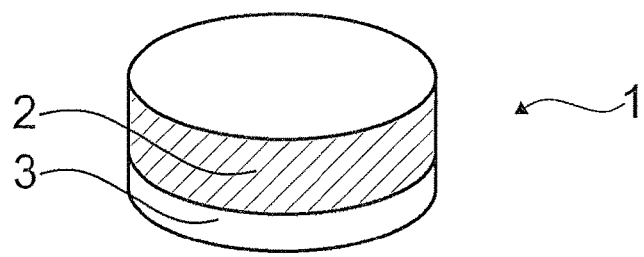
Fig. 2
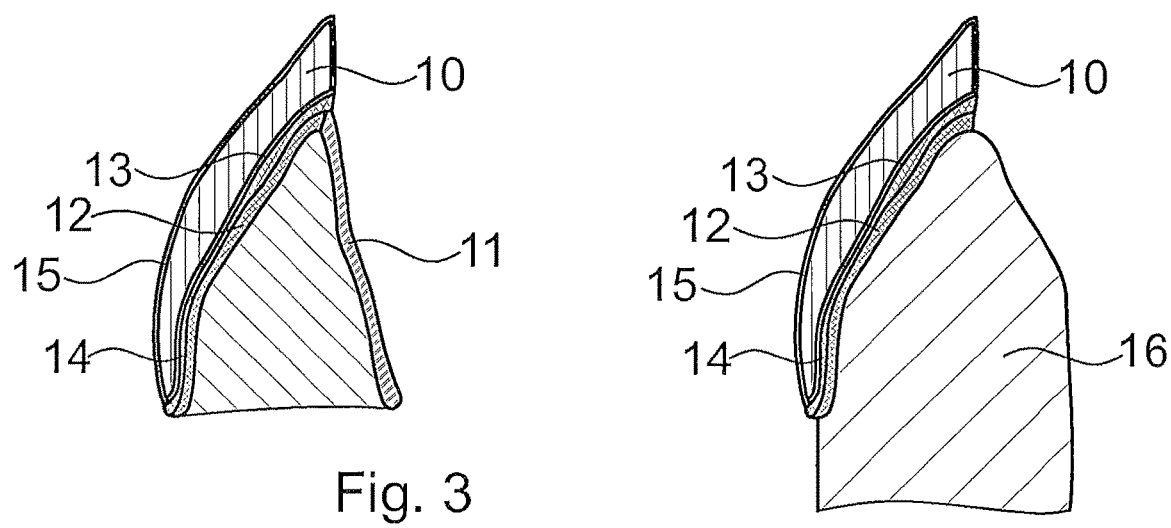
Fig. 3
Fig. 4

METHOD FOR PRODUCING DENTURES

CROSS REFERENCE TO RELATED APPLICATIONS

This application is the National Stage of PCT/EP2017/062469 filed on May 23, 2017, which claims priority under 35 U.S.C. § 119 of German Application Nos. 10 2016 109 447.1 filed on May 23, 2016 and 10 2016 109 449.8 filed May 23, 2018 the disclosures of which are incorporated by reference. The international application under PCT article 21(2) was not published in English.

BACKGROUND OF THE INVENTION

1. Field of the Invention

The invention relates to a method for the production of a dental prosthesis, in particular by means of a ceramic semi-finished product or by means of an anatomically shaped ceramic shell as a veneer of a dental framework or as a full ceramic dental prosthesis.

2. Description of the Related Art

Use of ceramic materials in dental technology is widespread. Aside from use in prosthetics, such as, for example, individual crowns, veneer shells (called veneers), for example, are also produced from ceramics.

A ceramic dental prosthesis and a method for its production are known from WO 2007/028 787 A1. In this document, a dental prosthesis is described, in particular in the form of a composite crown or a composite bridge, which prosthesis consists of two independent components, which are configured as an inner framework structure and an outer veneer sheath, which are connected with one another by means of a connector compound. In this regard, the connector compound is liquid or at least viscous at room temperature, so as to simplify processing. A method for the production of a functional dental element is known from DE 600 23 315 T2, in which method layers composed of a suitable ceramic material, which is a powder, are applied one after the other. In this regard, a binder is applied to each layer composed of powder at desired positions, by means of three-dimensional printing technology, so as to bind each layer composed of powder to the preceding layer, thereby allowing removal of excess, non-adhering powder. Subsequently, the dental element produced in this way is subjected to a sintering step, and the sintered element is infiltrated by a second phase. A debonding step can also follow the sintering step.

An adhesion-imparting agent between an oxide ceramic and a veneer material, in particular for dental purposes, is known from DE 10 2009 051 593 A1. In this regard, an adhesion-imparting agent in the form of a mixture of silicate ceramic and quartz is applied as a sol to a base body composed of an oxide ceramic or its starting materials, which body is to be veneered and has not yet been hard-sintered. Subsequently, the base body, with the adhesion-imparting agent worked into it, is completely sintered and afterward the veneer material is applied. In this way, dental crowns or bridges that can withstand great stress can be produced.

A green-ceramic tape is described in US 2004/0245663, which tape can be used for the production of dental restorations. For this purpose, the tape is laid around a model of a tooth stump and subsequently adjusted and fired.

A method for the production of a dental prosthesis is known from U.S. Pat. No. 5,346,397 A, in which method a ceramic shell that has not yet been adjusted and fired is used together with a ceramic paste as a buildup material, so that a dental prosthesis that matches in terms of color and shape but has not yet been fired is formed.

In EP 0 826 642 A2, the production of a ceramic dental prosthesis crown or of a ceramic dental prosthesis shell is described, in which a slip is shaped into a thin layer, this thin layer is applied to a plaster mold, dried layer by layer, and after application of all the required layers, the unfinished part is sintered.

Semi-finished products composed of ceramic materials are widespread in dental technology and up to the present have usually been used by means of CAD/CAM processing from densely sintered material, so as to be able to produce full ceramic dental prosthesis products.

A ceramic white compact for the production of a ceramic shaped part and a method for the production of a ceramic white compact are known from DE 10 2006 034 551 A1, wherein the ceramic white compact is formed by means of pre-sintering of a ceramic raw material that has been pressed to form a green compact, and this white compact, after sintering, is reinforced with an additional material to reinforce it, which material can be removed again, without residues, during subsequent treatment or processing of the white compact. The additional material is introduced into pores of the white compact in a state capable of flow, and subsequently hardened. This can be a polymer or a synthetic resin.

Semi-finished products known from technology are offered for sale as a white compact or in densely sintered form. Because of its very brittle structure, a white compact easily leads to spalling and cracking, and this makes chip-removing processing difficult and time-consuming. Densely sintered semi-finished products furthermore require special processing systems with cooling and additional grinding. Accordingly, such work is costly due to the special processing systems used for processing, and the risk of damage due to cracking or spalling is high. Furthermore, the processing times are very long.

SUMMARY OF THE INVENTION

It is the task of the invention to indicate a method for the production of a dental prosthesis, in which method easier processing is possible.

This task is accomplished by means of the characteristics of the invention. Further advantageous embodiments of the invention are discussed below. These can be combined with one another in technologically practical manner. The description, in particular in connection with the drawing, additionally characterizes and specifies the invention.

According to the invention, a method for the production of a dental prosthesis, in particular by means of ceramic semi-finished product or an anatomically shaped ceramic shell as a veneer of a dental framework or as a full ceramic dental prosthesis is indicated, which comprises the following steps: making available an anatomically shaped ceramic shell as a green compact; affixing the ceramic shell to a framework or to a carrier by means of a viscous ceramic filler compound as an equalization compound; and carrying out at least one firing step below a temperature of 1050° C.

The method according to the invention, for the production of a dental prosthesis, uses a green compact that can be shaped and therefore can be plastically adapted to the framework contour as a flexible veneer material.

According to one embodiment of the invention, adaptation of the anatomically shaped ceramic shell to the framework or of the carrier is additionally carried out.

According to a further embodiment of the invention, the ceramic filler compound has a color-imparting property.

According to a further embodiment of the invention, the step of making an anatomically shaped ceramic shell available comprises chip-removing processing of a semi-finished product, which is produced as a green compact from a mixture comprising a ceramic powder and a binder system.

According to a further embodiment of the invention, the step of making an anatomically shaped ceramic shell available comprises making a ceramic slip available, treating the ceramic slip to produce a slip film, possibly pre-drying the slip film to adjust the degree of moisture or the viscosity, forming a concave flexible ceramic shell in an anatomical shape, and removing the flexible ceramic shell in the form of a green compact.

According to a further embodiment of the invention, pressing the slip film into a negative mold, deep-drawing or introduction into mold plates takes place to form the concave ceramic shell.

According to a further embodiment of the invention, forming the concave ceramic shell takes place by means of a 3D printing process.

According to a further embodiment of the invention, the step of making an anatomically shaped ceramic shell available takes place with at least two differently colored layers.

According to a further embodiment of the invention, the green compact or the white compact that proceeds from the green compact is infiltrated.

According to a further embodiment of the invention, infiltration takes place with a glass or ceramic suspension, before the firing step.

According to a further embodiment of the invention, infiltration takes place by means of a polymer or resin, after the firing step.

According to a further embodiment of the invention, a firing step is carried out for the purpose of dense-sintering.

Use of a ceramic semi-finished product and chip-removing processing, or of a ceramic shell having an external shape that has already been formed is well suited, with regard to dimensional stability or precise fit, for the production of a dental prosthesis, wherein other methods, such as additive production shaping of ceramic restorations, for example, are also possible. In particular with a viscous ceramic filler compound that is adapted to the heat expansion coefficient and the shrinkage behavior, it is possible to equalize and thereby correct possible design errors within the CAD or processing errors of the chip-removing process before dense-sintering.

In this regard, in use, the viscous filler compound is injected behind the green compact or the white compact that proceeds from it, before dense-sintering, and the compact is then set back onto the dental framework or the support (for example a refractory compound) in the correct position. Here, the viscous filler compound (ceramic/glass sol) is supposed to equalize uneven gap dimensions or undercuts of the framework or of the shaped body made available as a refractory compound, so as to prevent the collapse locations on the veneer that are caused by them.

Because of its plastic deformability, clearly shorter processing times and a low tendency to cracks or fractures occur. The property of plastic deformability results in significant advantages in subsequent manual corrective shape adjustment to the carrier or framework. Because of the green processing that is possible here, shorter processing times of chip-removing cutting occur, since the green compact does not have the brittleness of white compacts or densely sintered semi-finished products, and therefore can be processed with faster processing parameters of chip-removing cutting (speed of rotation/advance/attack angle). The green compact can be processed dry on all machine systems. Accordingly, a ceramic semi-finished product for forming a chip-cut ceramic restoration is used, wherein subsequently, after the chip-removing process, shape-correcting adaptation to the carrier, for example a dental framework or a refractory shaped body, is possible. Accordingly, an adjustment, as it frequently needs to be undertaken in dental technology, is easily possible, since the ceramic shell can still be shaped and bent after the chip-removing process. This is made possible by means of the addition of binder to the green compact. The semi-finished product can be made available as a milled blank, for example with a diameter of 100 mm and a thickness of 14 mm. In this regard, a ceramic slip with a binder system is used, wherein the ceramic slip is prepared from ceramic material usual in dentistry, in corresponding paste-like form. Chip-removing processing of a green compact is possible without great effort, and does not make any special demands with regard to the tool to be used. Accordingly, simple but reliable processing is possible, which has faster processing times and simultaneously lower likelihood of fractures, spalling or cracking during the chip-removing process.

The green compact can be monochrome, so that a dental prosthesis can be formed that is provided with a single coloration. However, multiple layers of the green compact can also have different colors.

Accordingly, it is possible to adapt the coloration of the ceramic semi-finished product accordingly, so as to be able to correspondingly adjust color differences between the enamel and dentin region of a veneer shell accordingly, for example. In this regard, the different layers of the green compact are cast one after the other, for example, wherein partial drying of the already existing slip layer takes place between application of the subsequent layer, so as to be able to case a layer that lies above it separately. If necessary, a subsequent pressing process or a pressure treatment by means of subsequent post-compaction, by means of a pressure chamber or excess pressure, might be required, so as to better connect the boundary surfaces of the individual layers and to achieve lower shrinkage. In this regard, a uni-axial, biaxial or isostatic pressing method, in particular, could be used.

According to a further embodiment of the invention, the green compact or a white compact that results from the green compact is infiltrated. In this regard, infiltration can take place before or after the firing step, with a glass or ceramic suspension as well as by means of a polymer or resin.

In this regard, a further important point in the development of ceramic dental prostheses can be seen in that the fundamental possibility exists of infiltration by means of glass, ceramic or resin, which infiltration can be carried out before or after a firing step. This is currently not possible with commercially available ceramics, since these are batched up in powder form with a water base. Due to the water saturation or solubility of an immediate infiltration, this is not possible. Also, porosities and homogeneities are so non-uniform that uniform coloration, for example, could not be achieved. An infiltration eliminates or minimizes possible porosity, and thereby the mechanical stability of the ceramic is clearly increased. If the infiltration is implemented by means of a glass/ceramic suspension, subsequent firing is required. The infiltration can also take place by means of a polymer or resin after firing of the ceramic, wherein further firing is no longer possible.

It is also provided, according to the invention, to create a chromatic coloration of the ceramic sol, in other words a tooth-colored, chromatic glass sol for color adaptation of the veneer shell. A particular feature here is that the color effect proceeds from the framework or carrier, and this corresponds to anatomical coloration. In contrast to this, in the state of the art a color layer is painted onto the surface of the anatomical outer surface after firing for the purpose of color adjustment.

BRIEF DESCRIPTION OF THE DRAWINGS

In the following, some exemplary embodiments will be explained in greater detail using the drawing. This shows:

FIG. 1 a ceramic semi-finished product according to a first embodiment of the invention, in a perspective side view, FIG. 2 a ceramic semi-finished product according to a second embodiment of the invention, in a perspective side view, FIG. 3 a ceramic shell produced from the semi-finished product, together with a veneer framework, and FIG. 4 a ceramic shell produced from the semi-finished product, together with a shaped body.

In the figures, the same or functionally equivalent components are provided with the same reference symbols.

DETAILED DESCRIPTION OF THE PREFERRED EMBODIMENTS

Making reference to FIG. 1, a ceramic semi-finished product 1 is shown in a perspective side view. The ceramic semi-finished product 1 is cast from ceramic powder with a binder system, as a ceramic slip, and can be worked by means of chip-removing processing of the green compact formed in this manner, to produce an adaptable ceramic shell that can be formed onto a carrier and plastically adjusted before a fire step below a temperature of 1050° C.

Making reference to FIG. 2, a second embodiment is shown. Here, milled blanks are made available as a ceramic semi-finished product 1, in which polychrome layers 2, 3 are formed separately, one after the other, wherein after each casting process, the ceramic slip layer is partially dried, so as to case a separate layer 2 that lies above it. In a variant of the method, a subsequent damp pressing process or compaction by means of compressed air or vibration can be carried out, so as to better connect the boundary surfaces of the layers 2, 3 and to achieve lower shrinkage here.

Thereby it is possible to shape individual veneer shells by means of chip-removing processing both from the monochrome blank according to FIG. 1 and from the polychrome blank according to FIG. 2, and to affix them to a veneer framework or to a refractory shape framework. In this regard, additional coloration can be created by means of a different ceramic filler compound, in terms of color. In this regard, connection between the veneer shells and the framework or the shaped body takes place in a firing process. In this regard, however, plastic shape-correcting adjustment is possible, since the veneer shell can still be shaped after the chip-removing process.

Instead of a ceramic semi-finished product 1, however, a ceramic shell can also be made available that was formed in anatomically correct shape. In this regard, reference is made to the previously unpublished application DE 10 2016 109 447.1 of the same applicant. Production of a ceramic shell using an additive method, for example using a 3D printing process, would also be possible.

Use of a flexible ceramic shell 10, which can be produced as described above, will be explained in greater detail below, making reference to FIG. 3.

In FIG. 3, a veneer framework 11 is shown schematically, which has a corresponding convex veneer surface 12. The ceramic shell 10 is set onto this convex veneer surface 12. The ceramic shell has a concave contact surface 13, wherein a gap 14 is present between the concave contact surface 13 and the convex veneer surface 12.

The side of the ceramic shell 10 that lies opposite the contact surface 13 represents the vestibular, anatomical tooth shape 15. The gap 14 between the convex veneer surface 12 of the veneer framework 11 and the concave contact surface 13 of the ceramic shell 10 is eliminated by means of a ceramic filler compound that is typically made available as a ceramic sol. In this regard, the viscous ceramic filler compound functions as an equalization compound, and can accordingly equalize different gap dimensions as well as undercuts between the ceramic shell 10 and the veneer framework 11. Here, the filler compound, i.e. the ceramic/glass sol, is supposed to equalize different gap dimensions or undercuts of the framework or of the shaped body as a refractory compound, so as to prevent collapse locations on the veneer or the outer surface of the anatomical tooth shape 15 caused in this way. For this purpose, the viscous ceramic filler compound is injected behind the ceramic shell 10 after shaping fitting to the veneer framework 11, and the shell is pressed onto the veneer framework 11, so that excess filler compound is pressed out.

Because of the flexible property of the ceramic shell 10, the shape progression can thereby be individually adjusted by means of bending and cutting, for example at the preparation boundary. However, it is important that an uncontrolled shape change of the vestibular, anatomical tooth shape 15 is prevented by means of the use of the viscous ceramic filler compound. An irregular gap 14 would be transferred to the vestibular anatomical tooth shape 15, so that the ceramic shell 10 used as a veneer shell would be attached to the veneer framework with a changed outer shape. Likewise, collapse locations could form on the dental veneer.

An undesirable thermal change in shape caused by melting and shrinking is compensated, to the greatest possible extent, by means of the viscous ceramic filler compound. In this regard, it can also be provided that UV initiators for light polymerization are added to the filler compound, so that until the first firing step, the ceramic shell 10 is fixed in place on the veneer framework 11, by way of the filler compound.

In FIG. 4, a second embodiment is shown. Here, in contrast to the embodiment according to FIG. 3 described above, the ceramic shell 10 is applied not to a veneer framework but rather to a refractory shaped body 16, for example in an application as a full ceramic restoration. However, further process management and attachment are identical.

Accordingly, the ceramic shell 10 can be used not only for forming a full ceramic dental prosthesis in the form of a crown or cap with a palatinal component, but also for placing a veneer on a dental framework.

After the first firing step, further firing steps for color correction and shape correction can also be carried out. The ceramic shell 10, produced as a film ceramic, is elastic and can therefore be individually adapted to the three-dimensional shape progression of the preparation boundary, by means of bending and cutting. It is fundamentally possible to add a suitable UV initiator for light polymerization to the ceramic sol, so as to fix the ceramic shell 10, which has been subsequently adapted to the framework or carrier in terms of its shape, in place until the first firing.

The remaining free surfaces of the framework can subsequently be conventionally provided with a veneer using a conventional powder ceramic/water mixture and a ceramic brush, or they can be completed using a thixotropic ceramic sol, to provide the desired tooth shape.

Since shrinkage of up to 16% can be assumed during the first main vacuum firing, the approximal regions and the incisal strip can be built up using suitable effect compounds, so as to compensate for this shrinkage within the scope of the first firing, together with the green compact.

Furthermore, use of the industrially produced flexible ceramic shell offers the significant advantage of the very homogeneous ceramic structure, which leads to uniform shrinkage. In contrast to this, manual anatomical layering demonstrates the significant disadvantage that here, a powder ceramic that is mixed with different viscosity and solid/water content, in portions, is used, and this then leads to differently great shrinkage and crack formation.

The characteristics indicated above, as well as the characteristics that can be derived from the figures, can be advantageously implemented both individually and in different combinations. The invention is not restricted to the exemplary embodiments described, but rather can be modified in many ways within the scope of the ability of a person skilled in the art.

The invention claimed is:

1. A method for the production of a dental prosthesis, comprising the steps:
    making available an adaptable anatomically shaped ceramic shell having a contact surface and an opposing outer surface of a vestibular, anatomical tooth form as a plastically adaptable green compact;
    plastically adapting the anatomically shaped ceramic shell to a framework or a carrier, and affixing the ceramic shell to the framework or to the carrier by means of a viscous ceramic filler compound as an equalization compound; and
    carrying out at least one firing step below a temperature of 1050° C.

2. The method according to claim 1, in which the ceramic filler compound has a color-imparting property.

3. The method according to claim 1, in which the step of making an anatomically shaped ceramic shell available comprises chip-removing processing of a ceramic semi-finished product, which is produced as the green compact from a mixture comprising a ceramic powder and a binder system.

4. The method according to claim 1, in which the step of making an anatomically shaped ceramic shell available comprises making a ceramic slip available, treating the ceramic slip to produce a slip film, optionally pre-drying the slip film to adjust the degree of moisture or the viscosity, forming a concave flexible ceramic shell in an anatomical shape, and removing the flexible ceramic shell in the form of the green compact.

5. The method according to claim 4, in which pressing the slip film into a negative mold, deep-drawing or introduction into mold plates takes place to form the concave ceramic shell.

6. The method according to claim 1, in which forming the anatomically shaped ceramic shell takes place by means of an additive method or milling process.

7. The method according to claim 1, in which the step of making an anatomically shaped ceramic shell available takes place with at least two differently colored layers.

8. The method according to claim 1, in which the green compact or a white compact that proceeds from the green compact is infiltrated.

9. The method according to claim 8, in which infiltration takes place with a glass or ceramic suspension, before the at least one firing step.

10. The method according to claim 8, in which infiltration takes place by means of a polymer or resin, after the at least one firing step.

11. The method according to claim 1, in which a firing step for dense-sintering is carried out.

12. The method according to claim 1, in which the ceramic shell is structured as a veneer shell.

13. The method according to claim 1, in which the ceramic shell is structured as a cap or crown with a palatinal component.

* * * * *